United States Patent
Borycki et al.

(10) Patent No.: US 9,186,057 B2
(45) Date of Patent: Nov. 17, 2015

(54) OPTICAL COHERENCE TOMOGRAPHIC IMAGING APPARATUS AND CONTROL METHOD THEREOF

(71) Applicant: CANON KABUSHIKI KAISHA, Tokyo (JP)

(72) Inventors: Dawid Borycki, Toruń (PL); Yasuhiro Nakahara, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 13/967,328

(22) Filed: Aug. 14, 2013

(65) Prior Publication Data

US 2014/0063507 A1 Mar. 6, 2014

(30) Foreign Application Priority Data

Aug. 30, 2012 (JP) ................................. 2012-190616

(51) Int. Cl.
  *G01B 9/02* (2006.01)
  *A61B 3/10* (2006.01)
  *A61B 3/14* (2006.01)

(52) U.S. Cl.
  CPC ............... *A61B 3/102* (2013.01); *A61B 3/1025* (2013.01); *A61B 3/14* (2013.01); *G01B 9/02091* (2013.01)

(58) Field of Classification Search
  CPC .. G01B 9/02091; A61B 3/102; A61B 3/1025; A61B 3/14
  See application file for complete search history.

(56) References Cited

U.S. PATENT DOCUMENTS

| | | | |
|---|---|---|---|
| 7,980,696 B1 * | 7/2011 | Taki et al. ..................... | 351/206 |
| 8,771,261 B2 * | 7/2014 | Andersen et al. ................ | 606/4 |
| 2006/0170930 A1 | 8/2006 | Li | |
| 2007/0222945 A1 * | 9/2007 | Tsukada et al. ............... | 351/205 |
| 2012/0188510 A1 * | 7/2012 | Suehira et al. ................ | 351/208 |
| 2012/0249963 A1 * | 10/2012 | Yoshida ........................ | 351/208 |

FOREIGN PATENT DOCUMENTS

| | | |
|---|---|---|
| CN | 102551654 A | 7/2012 |
| EP | 2130486 A1 | 12/2009 |
| EP | 2638849 A1 | 9/2013 |
| JP | 2009-291252 A | 12/2009 |

(Continued)

OTHER PUBLICATIONS

Extended European search report issued on Dec. 10, 2013, in counterpart European Patent Application No. 13182015.1.

(Continued)

*Primary Examiner* — Michael A Lyons
(74) *Attorney, Agent, or Firm* — Carter, DeLuca, Farrell & Schmidt, LLP

(57) ABSTRACT

An optical coherence tomographic imaging apparatus capable of shortening the time required for focus adjustment and reducing the burden on an object is provided. The apparatus includes a first focus unit that moves a first optical focus member disposed in a light-receiving optical system of an optical observation system that obtains an observed image of an object, and a second focus unit that moves a second optical focus member disposed in an optical interference system that acquires a tomographic image of the object in conjunction with a movement of the first optical focus member.

30 Claims, 7 Drawing Sheets

(56) References Cited

FOREIGN PATENT DOCUMENTS

| | | |
|---|---|---|
| JP | 2010-012109 A | 1/2010 |
| JP | 2010-035949 A | 2/2010 |

OTHER PUBLICATIONS

Chinese Office Action issued in corresponding application No. 201310388814.2 on Feb. 12, 2015.

* cited by examiner

OPTICAL COHERENCE TOMOGRAPHIC IMAGING APPARATUS AND CONTROL METHOD THEREOF

BACKGROUND OF THE INVENTION

1. Field of the Invention

The present invention relates to an optical coherence tomographic imaging apparatus used for ophthalmic care and the like.

2. Description of the Related Art

Currently, various ophthalmic apparatuses using optical apparatuses are known. For example, various apparatuses such as an anterior ocular segment imaging apparatus, fundus camera, and SLO (Scanning Laser Ophthalmoscope) are used as apparatuses for the observation of the eyes. Among these apparatuses, an optical tomographic imaging apparatus based on OCT (Optical Coherence Tomography) using multi-wavelength light wave coherence can obtain a tomographic image of a sample at high resolution. The apparatus is becoming indispensable to outpatient clinics specialized in retinas as an ophthalmic apparatus. This apparatus will be referred to as an OCT apparatus hereinafter.

An OCT apparatus irradiates a sample with measurement light which is low-coherence light, and can perform high-sensitivity measurement of backscattered light from the sample by using an interference system or optical interference system. Low-coherence light has the property of being able to obtain a high-resolution tomographic image by increasing the wavelength width. In addition, the OCT apparatus can obtain a high-resolution tomographic image by scanning measurement light on a sample. Therefore, the OCT apparatus can acquire a tomographic image of the retina at the fundus of an eye to be examined, and hence has been widely used for ophthalmic care and the like for the retina.

On the other hand, the OCT apparatus as an ophthalmic apparatus is generally equipped with optical systems for fundus observation, anterior eye observation, and the like to implement alignment adjustment between the apparatus and an eye to be examined. Japanese Patent Laid-Open No. 2009-291252 discloses an ophthalmic apparatuses that performs primary focusing (rough focus) of the focus lens of an OCT optical system for acquiring a tomographic image based on the focus position of the focus lens of the SLO optical system for fundus observation. The ophthalmic apparatuses disclosed in Japanese Patent Laid-Open No. 2009-291252 starts moving the focus lens of the OCT optical system to the primary focus position after the movement of the focus lens of the SLO optical system to the focus position has ended.

If focus adjustment takes long time, the burden on the subject increases.

SUMMARY OF THE INVENTION

The present invention provides an optical coherence tomographic imaging apparatus capable of shortening the time required for focus adjustment and thus reducing the burden on a subject.

An optical coherence tomographic imaging apparatus according to an aspect of the present invention includes an optical interference system that acquires a tomographic image of an object based on interference light between return light from the object irradiated with measurement light and reference light corresponding to the measurement light, an optical observation system that includes an optical illumination system that illuminates the object and a light-receiving optical system that causes a light-receiving element to receive the return light from the object, and obtains an observed image of the object based on a light reception signal output from the light-receiving element, a first focus unit configured to move a first optical focus member disposed in the light-receiving optical system, and a second focus unit configured to move a second optical focus member disposed in the optical interference system in conjunction with a movement of the first optical focus member.

Further features of the present invention will become apparent from the following description of exemplary embodiments (with reference to the attached drawings).

DESCRIPTION OF THE EMBODIMENTS

An embodiment of the present invention will now be described in detail with reference to the accompanying drawings. Note that the present invention is not limited to the embodiment to be described below, which is merely a detailed example advantageous for practice of the present invention. In addition, not all the combinations of features described in the following embodiment are essential for the solution to the problem that is provided by the present invention.

In the following embodiment, an optical coherence tomographic imaging apparatus (OCT apparatus) to which the present invention is applied will be described.

(Schematic Arrangement of Apparatus)

Figure 1:
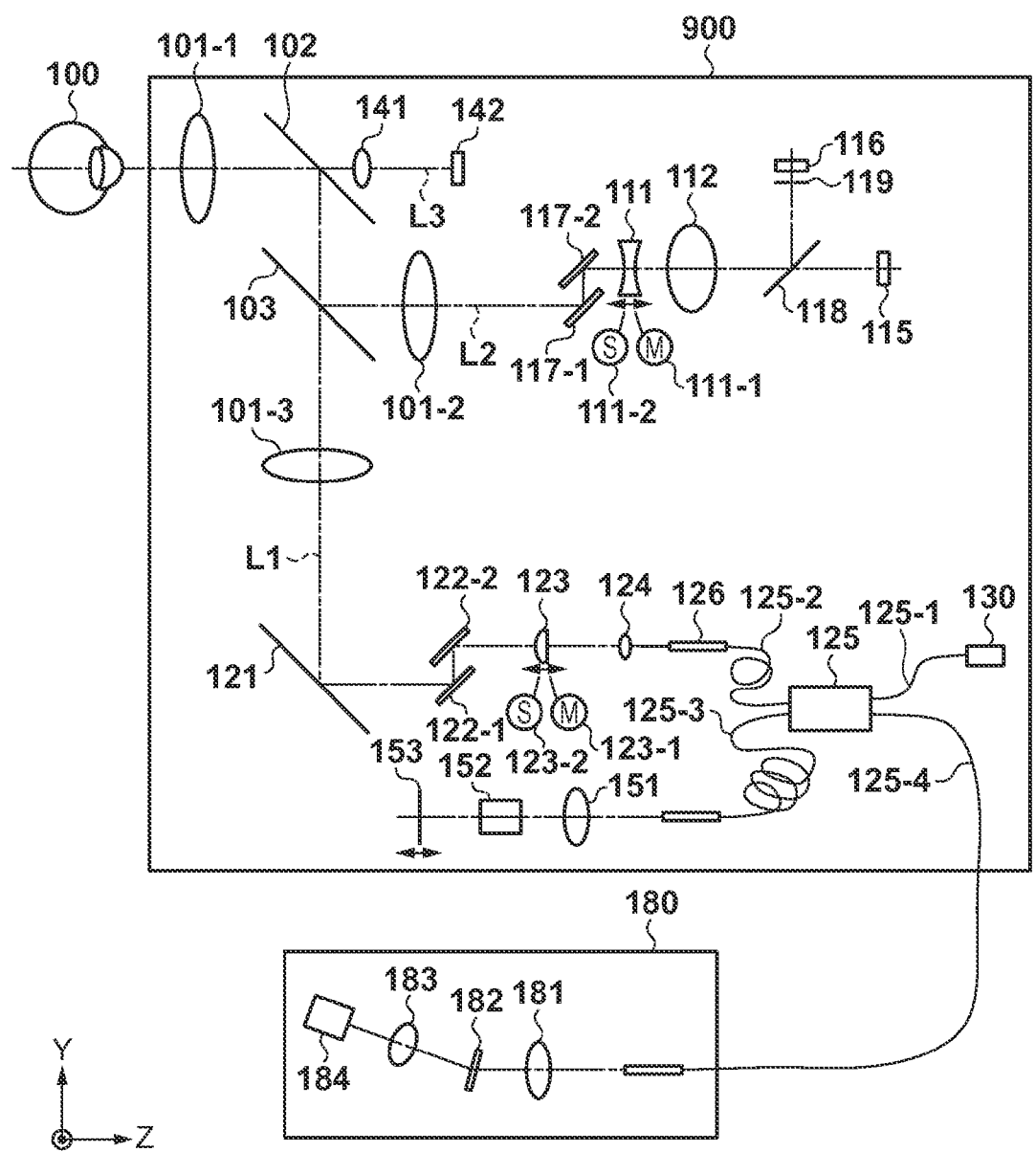
FIG. 1 is a view showing the schematic arrangement of a funduscopy apparatus according to the embodiment.

FIG. 1 is a view showing the arrangement of a funduscopy apparatus that is an example of the optical coherence tomographic imaging apparatus. Referring to FIG. 1, an optical head 900 is formed by a measurement optical system for capturing an anterior eye image of an eye to be examined, which is an example of an object, and a two-dimensional image and tomographic image of the fundus.

The arrangements of the measurement optical system and a spectrometer according to this embodiment will be described with reference to FIG. 1.

The internal arrangement of the optical head 900 will be described first. An objective lens 101-1 is disposed to face an eye 100 to be examined. On the optical axis of this lens, a first dichroic mirror 102 and a second dichroic mirror 103 divide the optical path. That is, they divide the optical path for each wavelength band into a measurement optical path L1 of an OCT optical system (optical interference system), a fundus optical observation path/fixation lamp optical path L2, and an anterior ocular segment optical observation path L3. Reference numerals 101-2, 111, and 112 denote lenses. A stepping motor 111-1 is for moving the lens 111 to the focus position. The lens 111 is an example of a first optical focus member used for focus adjustment of the fixation lamp and fundus observation, and is driven by the stepping motor 111-1. A photo interrupt sensor (PI sensor) 111-2 calibrates the origin of the stepping motor 111-1.

The optical path L2 constitutes an SLO optical system (optical observation system). More specifically, the optical path L2 includes an optical illumination system that irradiates the fundus of the eye to be examined with illumination light, and a light-receiving optical system that causes a light-receiving element to receive fundus reflected light (return light). The optical path L2 is configured to obtain the front fundus image (observed image) of the eye to be examined based on a light reception signal output from the light-receiving element. More specifically, the fundus optical observation system includes an X scanner and a Y scanner and is configured to obtain a two-dimensional fundus image by scanning a spot on the fundus. A light source 115 generates light having a wavelength of, for example, 780 nm. An X scanner 117-1 and a Y scanner 117-2 which serve to scan the light generated by the light source 115 on the fundus of the eye 100 are disposed. The lens 101-2 is disposed such that its focal position is located near the central position between an X scanner 117-1 and a Y scanner 117-2. The X scanner 117-1 is formed from a polygon mirror to scan in the X direction at high speed. The X scanner 117-1 may be formed from a resonance mirror. A signal detector 116 is a light-receiving element that is formed from an APD (avalanche photodiode) and detects light (fundus reflected light) scattered/reflected by the fundus. A pinhole plate 119 is disposed immediately before the single detector 116. Hence, light of the maximum amount reaches the single detector 116 in a focus state. A prism 118 is a prism on which a perforated mirror or hollow mirror is deposited, and separates illumination light emitted by the light source 115 and return light from the fundus.

A lens 141 and an infrared CCD 142 for anterior eye observation are disposed on the optical path L3. The infrared CCD 142 has sensitivity near the wavelength of anterior eye observation illumination light (not shown), more specifically, 970 nm.

The optical path L1 forms an OCT optical system (optical interference system) used to capture a tomographic image of the fundus of the eye 100, as described above. A lens 101-3, a mirror 121, and the X scanner 122-1 and Y scanner 122-2 which serve as scanning units for scanning measurement light emitted by a light source for generating a low-coherent light on the fundus of the eye 100 are disposed on the optical path L1. Reference light (reference light corresponding to measurement light) generated by light emitted by the light source and fundus reflected light (return light) based on the measurement light that has irradiated the fundus of the eye are combined, and thus obtained interference light is received, thereby obtaining a tomographic image of the fundus of the eye. The scanner central position between the X scanner 122-1 and the Y scanner 122-2 is conjugate to the pupil position of the eye 100. The lens 101-3 and the scanner central position are disposed so as to make a light beam between the lens 101-1 and the lens 101-3 almost parallel. According to this arrangement, the optical path from the X scanner 122-1 and the Y scanner 122-2 becomes almost parallel between the lens 101-1 and the lens 101-3. This can make the incident angle of light on the first dichroic mirror 102 coincide with that on the second dichroic mirror 103 even when the X scanner 122-1 and the Y scanner 122-2 perform scanning.

A measurement light source 126 is a light source for measurement light which makes measurement light enter a measurement optical path. In this embodiment, the measurement light source 126 is disposed on a fiber end and optically conjugate to the fundus region of the eye 100. Reference numerals 123 and 124 denote lenses. A stepping motor 123-1 is for moving the lens 123. The lens 123 is an example of a second optical focus member used for focus adjustment, and is driven by the stepping motor 123-1. A PI sensor 123-2 calibrates the origin of the stepping motor 123-1.

Focus adjustment is performed so as to form an image of light emitted by the measurement light source 126 on the fiber end on the fundus of the eye 100. The lens 123 is disposed between the measurement light source 126 and the X scanner 122-1 and Y scanner 122-2. This makes it unnecessary to move the larger lens 101-3 or a fiber 125-2.

This focus adjustment makes it possible to form an image of the measurement light source 126 on the fundus of the eye 100 and efficiently return return light from the fundus of the eye 100 to the fiber 125-2 through the measurement light source 126.

In FIG. 1, the optical path between the X scanner 122-1 and the Y scanner 122-2 is formed within the drawing surface. In fact, the optical path is formed in a direction perpendicular to the drawing surface. In this embodiment, the SLO optical system and the OCT optical system are of a point scan type that two-dimensionally scans using two scanners. Instead of this scan type, for example, a line scan type that one-dimensionally scans a line beam is also applicable. A full field type that captures an image at once using an area sensor without scan is also applicable.

The arrangements of the optical path from a light source 130, a reference optical system, and a spectrometer will be described next.

Reference numeral 130 denotes the light source; 153, a mirror; 152, a dispersion-compensating glass; 125, an optical coupler; 125-1 to 125-4, single-mode optical fibers connected to the optical coupler so as to be integrated; 151, a lens; and 180, a spectrometer.

These components constitute a Michelson interferometer system. Light emitted by the light source 130 passes through the optical fiber 125-1 and is divided through the optical coupler 125 into measurement light on the side of the optical fiber 125-2 and reference light on the side of the optical fiber 125-3. The measurement light passes through the above-described optical path of the OCT optical system, irradiates the fundus of the eye 100 as an observation target, and reaches the optical coupler 125 through the same optical path by reflection and scattering by the retina.

On the other hand, the reference light reaches and is reflected by the mirror 153 through the optical fiber 125-3, the lens 151, and the dispersion-compensating glass 152 inserted to match the dispersion of the measurement light with that of the reference light. This light then returns along the same optical path and reaches the optical coupler 125. The optical coupler 125 combines the measurement light and the reference light to form interference light. In this case, interference occurs when the optical path length of the measurement light becomes almost equal to that of the reference light. A motor and a driving mechanism (neither are shown) hold the mirror 153 so as to adjust its position in the optical axis direction, thereby matching the optical path length of the measurement light, which changes depending on the eye 100, with that of the reference light. The interference light is guided to the spectrometer 180 through the optical fiber 125-4.

The spectrometer 180 includes lenses 181 and 183, a diffraction grating 182, and a line sensor 184. The interference light emerging from the optical fiber 125-4 is made almost parallel through the lens 181, and then spectroscoped by the diffraction grating 182. The lens 183 forms the light into an image on the line sensor 184.

The periphery of the light source 130 will be described next. The light source 130 is an SLD (Super Luminescent Diode) which is a typical low-coherent light source. The center wavelength is 855 nm, and the wavelength bandwidth is about 100 nm. The bandwidth is an important parameter which influences the resolution of an obtained tomographic image in the optical axis direction. An SLD is selected as the light source. However, ASE (Amplified Spontaneous Emission) or the like may be used as long as it can emit low-coherent light. In consideration of measurement of an eye, the wavelength of infrared light is suitable as the center wavelength. In addition, the center wavelength influences the resolution of an obtained tomographic image in the horizontal direction and is therefore preferably as short as possible. For the two reasons, the center wavelength is set to 855 nm.

Although this embodiment uses a Michelson interferometer as an interferometer, a Mach-Zehnder interferometer may be used. It is preferable to use a Mach-Zehnder interferometer when the light amount difference between measurement light and reference light is large, and a Michelson interferometer when the light amount difference is relatively small.

(Details of SLO Focus Driving Unit and OCT Focus Driving Unit)

Figure 2:
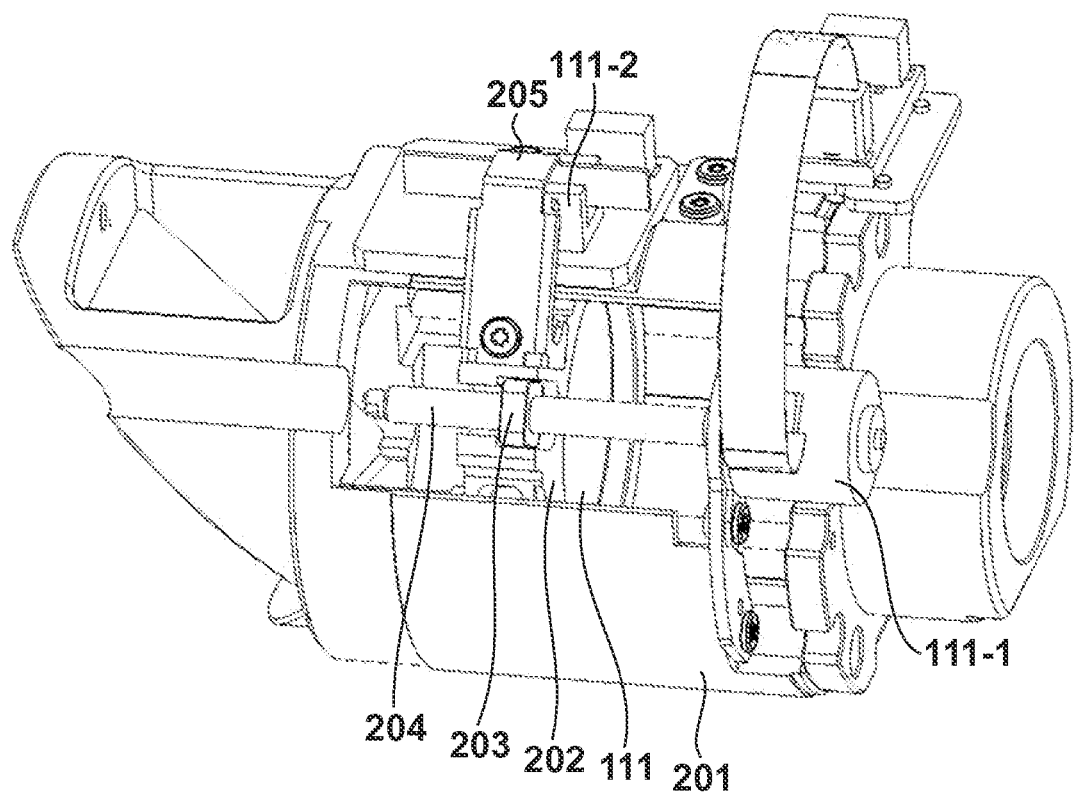
FIG. 2 is a perspective view showing the main part of an optical head so as to explain the SLO focus driving unit of the funduscopy apparatus according to the embodiment.

Details of the SLO focus driving unit will be described with reference to FIG. 2. The stepping motor 111-1 drives the lens 111 for SLO focus adjustment by, for example, 1.8° (diopter) in every step.

Reference numeral 111-2 denotes the PI sensor. An SLO focus base 201 is a base component that holds the lens 111 for SLO focus adjustment and a mechanism for driving the lens 111. The lens 111 for SLO focus adjustment is fixed in a frame component 202. Reference numeral 203 denotes a nut. A feed screw 204 has a pitch of 0.5 and is press-fitted and fixed in the shaft of the stepping motor 111-1. The frame component 202 is fitted on a shaft guide parallel to the feed screw 204 fixed on an SLO focus base (not shown). A coil spring (not shown) is inserted in the shaft guide to always bring the nut 203 and the frame component 202 in tight contact with each other. A slit washer 205 is fixed to the frame component 202 by screws and moves interlockingly with the frame component. The slit washer 205 is inserted between the light-emitting unit and the light-receiving unit (neither are shown) of the PI sensor 111-2. The slit washer turns on/off the PI sensor, thereby calibrating the pulse position and physical position of the stepping motor 111-1.

Figure 3:
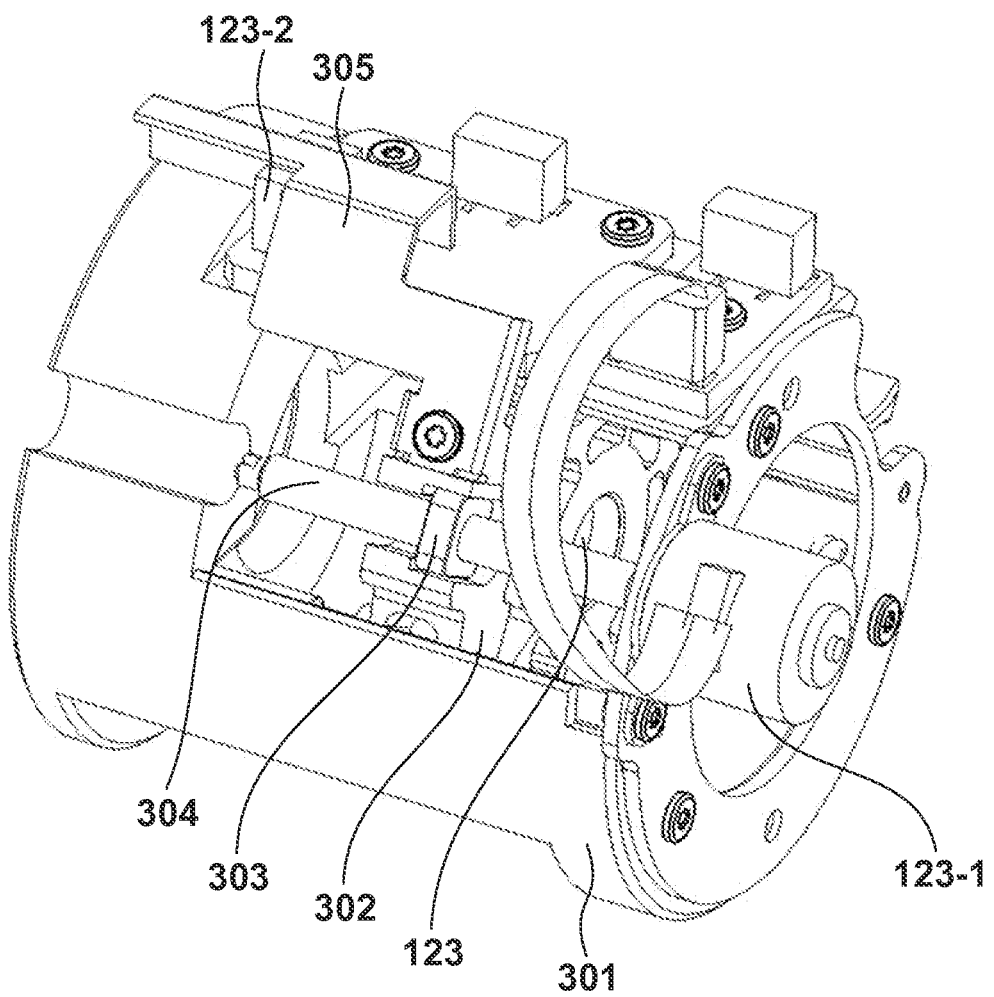
FIG. 3 is a perspective view showing the main part of the optical head so as to explain the OCT focus driving unit of the funduscopy apparatus according to the embodiment.

Details of the OCT focus driving unit will be described next with reference to FIG. 3. The stepping motor 123-1 drives the lens 123 for OCT focus adjustment by, for example, 1.8° (diopter) in every step.

Reference numeral 123-2 denotes the PI sensor. An OCT focus base 301 is a base component that holds the lens 123 for OCT focus adjustment and a mechanism for driving the lens 123. The lens 123 for OCT focus adjustment is fixed in a frame component 302. Reference numeral 303 denotes a nut. A feed screw 304 has a pitch of 0.5 and is press-fitted and fixed in the shaft of the stepping motor 123-1. The frame component 302 is fitted on a shaft guide parallel to the feed screw 304 fixed on an SLO focus base (not shown). A coil spring (not shown) is inserted in the shaft guide to always bring the nut 303 and the frame component 302 in tight contact with each other. A slit washer 305 is fixed to the frame component 302 by screws and moves interlockingly with the frame component. The slit washer 305 is inserted between the light-emitting unit and the light-receiving unit (neither are shown) of the PI sensor 123-2. The slit washer turns on/off the PI sensor, thereby calibrating the pulse position and physical position of the stepping motor 123-1.

(Moving OCT Focus Lens Based on Position Information of SLO Focus Lens)

Figure 4:
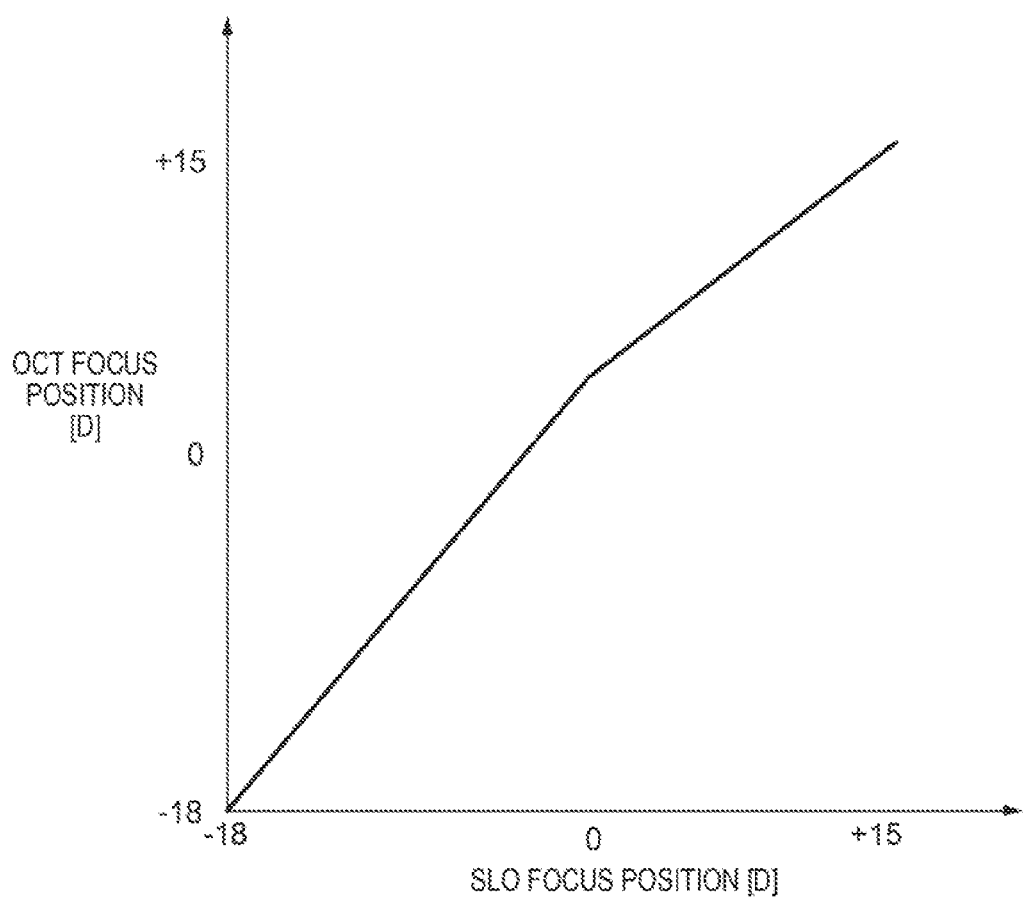
FIG. 4 is a graph showing the correlation between the SLO focus position and the OCT focus position.

A case will be explained next with reference to FIG. 4 and the like, in which the OCT focus lens (the focus lens of the OCT optical system) is moved based on the position information of the SLO focus lens (the focus lens of the SLO optical system). FIG. 4 is a graph showing the correlation between the SLO focus position and the OCT focus position. In this embodiment, first, the position information of the OCT focus lens is acquired based on the position information of the SLO focus lens in accordance with the correlation shown in FIG. 4. The OCT focus lens is moved based on the acquired position information. Each position information is represented by diopter (to be referred to as D hereinafter). Letting X be the value D on the SLO side, and Y be the value D on the OCT side, relations given by $$Y=0.76X+3.6 (0<X<15) \quad (1)$$

$$Y=1.2X+3.6 (-18<X<0) \quad (2)$$

hold.

Figure 5:
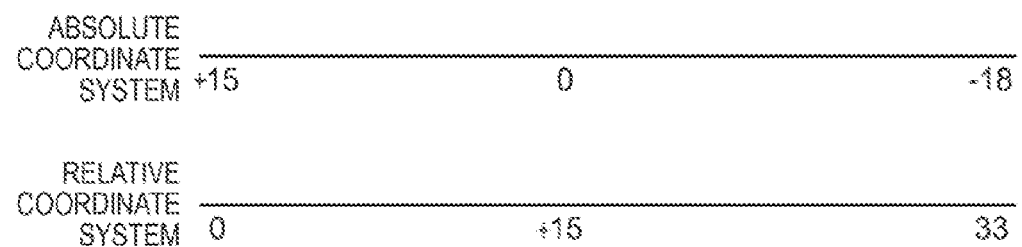
FIG. 5 is a view showing comparison between the absolute coordinate system and the relative coordinate system of SLO and OCT.

FIG. 5 is a view showing a comparison between the absolute coordinate system and the relative coordinate system of SLO and OCT focus lenses. The SLO and OCT focus lenses operate within the range of +15D to −18D on the absolute coordinate system. In this embodiment, the origin is set at +15D for both SLO and OCT. For this reason, focus driving control is performed by replacing the coordinate system with a relative coordinate system in which 0D corresponds to +15D, and 33D corresponds to −18D.

The value D on the absolute coordinate system is defined as Dz, and the value D on the relative coordinate system is defined as Ds. The association of the values, which is common to SLO and OCT, can be expressed as $$Dz=-Ds+15 \quad (3)$$

$$Ds=-Dz+15 \quad (4)$$

Based on equation (3), when the value D on the relative coordinate system of SLO is known, the value D is defined as Dsx, and equations (1) and (2) are rewritten as $$Y=0.76(-Dsx+15)+3.6 (0<X<15) \quad (5)$$

$$Y=1.2(-Dsx+15)+3.6 (-18<X<0) \quad (6)$$

In addition, 1D and the pulse of the stepping motor hold a relation given by $$1[D]=260[P] \quad \text{(relation 1)}$$

(Procedure of Focus Adjustment)

Figure 6A:
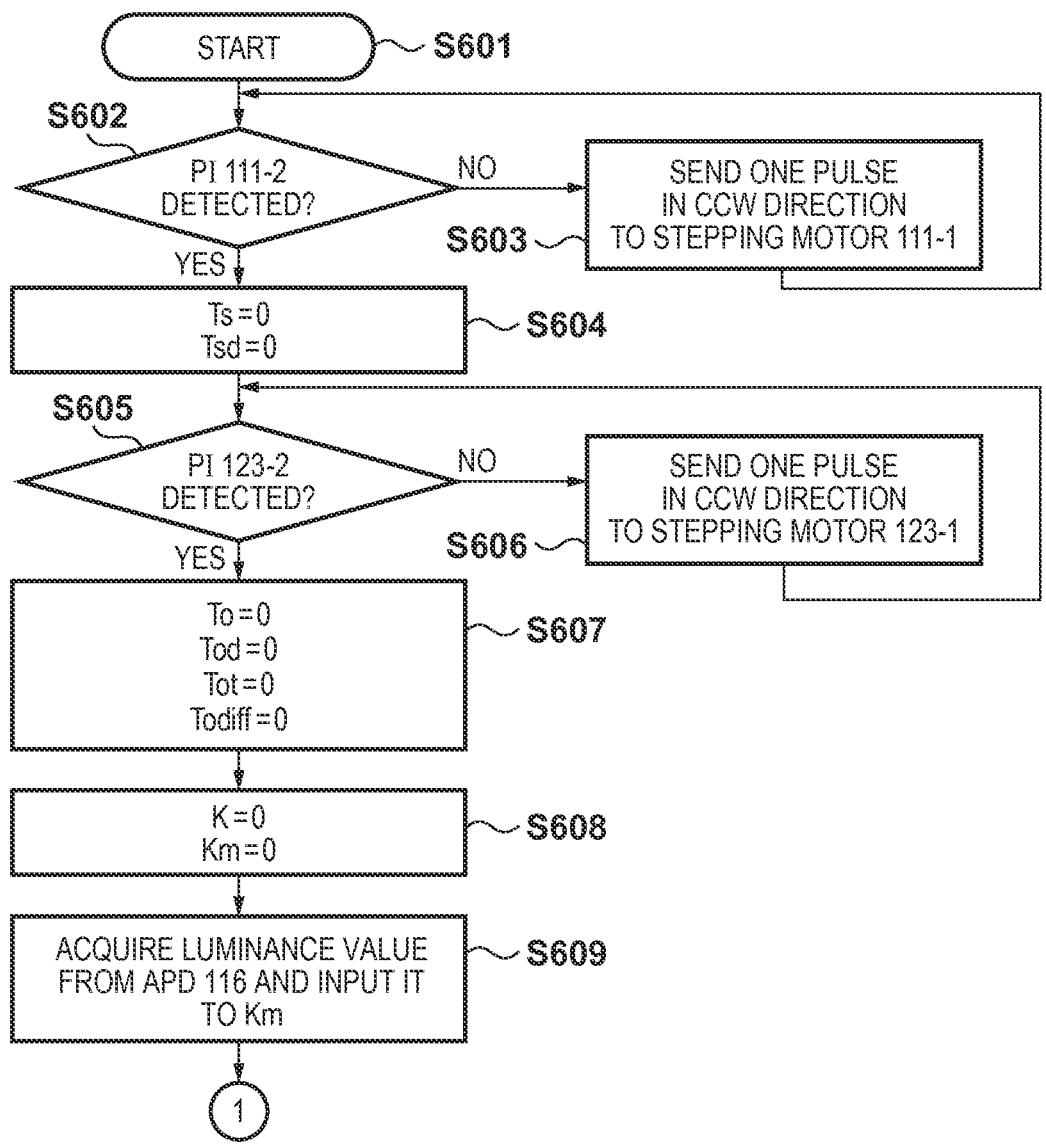
FIGS. 6A-6C are flowcharts showing control of SLO focus.
Figure 6B:
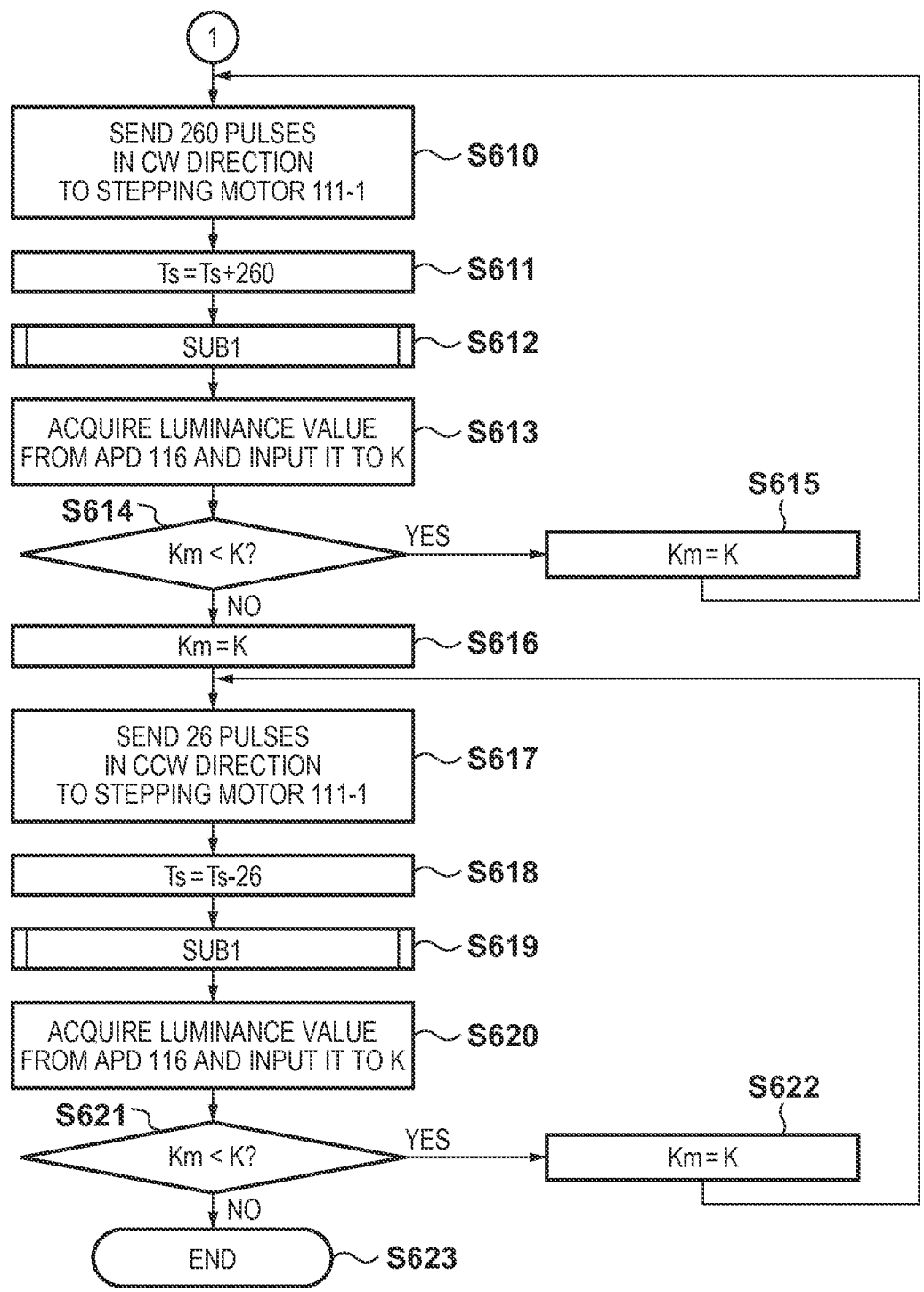
Figure 6C:
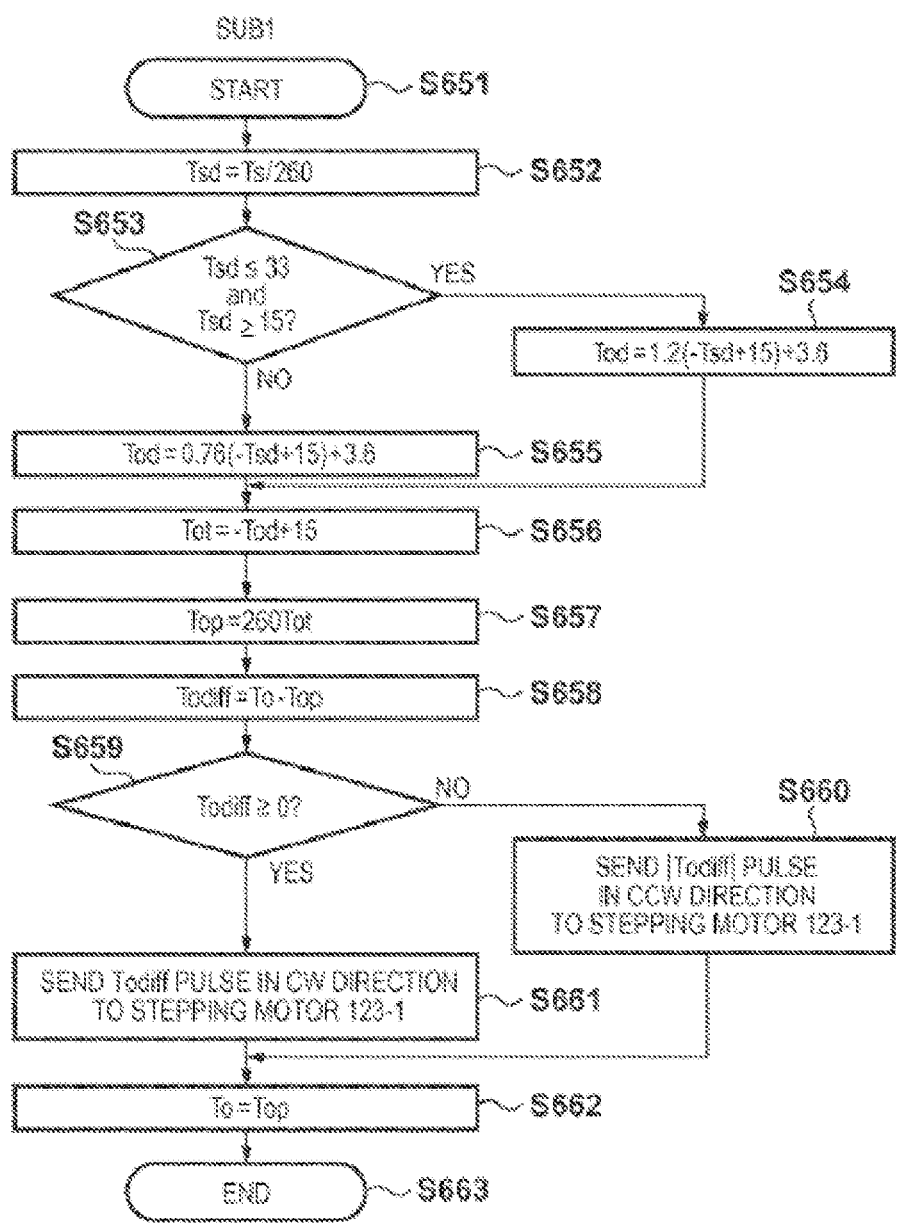

FIGS. 6A-C are flowcharts showing the procedure of the SLO focus including the behavior of the OCT focus.

The outline will be described first. Steps S602 to S608 correspond to the procedure of forming the pulse counter and actual position of the stepping motor of each of the SLO and OCT focus lenses. Steps S609 to S616 correspond to the procedure of rough SLO focus and the behavior of the OCT focus at that time. Steps S617 to S623 correspond to the procedure of fine SLO focus and the behavior of the OCT focus at that time.

The procedure will be explained below in order. In step S602, it is determined whether PI 111-2 is detected. If the PI 111-2 is not detected, the process advances to step S603. In step S603, one pulse in the CCW direction is sent to the stepping motor 111-1. The process then returns to step S602. Upon detecting the PI 111-2 in step S602, the process advances to step S604. In step S604, 0 is substituted into a variable Ts of the pulse counter value of the stepping motor 111-1 that drives the SLO focus and a variable Tsd of the value D on the relative coordinate system of SLO. The process advances to step S605.

In step S605, it is determined whether PI 123-2 is detected. If the PI 123-2 is not detected, the process advances to step S606. In step S606, one pulse in the CCW direction is sent to the stepping motor 123-1. The process then returns to step S605. Upon detecting the PI 123-2 in step S605, the process advances to step S607. In step S607, 0 is substituted into variables To, Tod, Tot, and Todiff. To is a variable representing the pulse counter value of the positioning target position of the OCT focus. Tod is a variable representing the value Y of equation (5) or (6). Tot is a variable representing the value Ds of equation (4). Todiff is a variable representing the pulse counter value difference between the current position and the positioning target position of the OCT focus. The process advances to step S608.

In step S608, 0 is substituted into variables K and Km of a luminance value. The process advances to step S609. In step S609, a luminance value is acquired from the APD 116 and substituted into Km. The process advances to step S610. In step S610, 260 pulses in the CW direction are sent to the stepping motor 111-1. The process advances to step S611. In step S611, 260 is added to Ts. The process advances to step S612.

Step S612 is defined processing SUB1 of moving the OCT focus in conjunction with the SLO focus. This will be described later in detail. The process advances to step S613.

In step S613, a luminance value is acquired from the APD 116 and substituted into K. The process advances to step S614. In step S614, it is determined whether Km is smaller than K. If Km is smaller than K, the process advances to step S615. In step S615, the value K is substituted into Km. The process then returns to step S610. With the loop of steps S610 to S615, the rough peak position of the luminance of the APD, that is, the rough SLO focus position is obtained. If Km is not smaller than K, the process advances to step S616. In step S616, the value K is substituted into Km. The process advances to step S617.

In step S617, 26 pulses in the CCW direction are sent to the stepping motor 111-1. The process advances to step S618. In step S618, 26 is subtracted from Ts. The process advances to step S619.

Step S619 is defined processing SUB1 of moving the OCT focus in conjunction with the SLO focus. This will be described later in detail. The process advances to step S620. In step S620, a luminance value is acquired from the APD 116 and substituted into K. The process advances to step S621.

In step S621, it is determined whether Km is smaller than K. If Km is smaller than K, the process advances to step S622. In step S622, the value K is substituted into Km. The process then returns to step S617. With the loop of steps S617 to S622, the fine peak position of the luminance of the APD, that is, the fine SLO focus position is obtained. If Km is not smaller than K, the process advances to step S623. In step 3623, the procedure ends.

Details of the defined processing SUB1 in steps S612 and S619 will be described next. In step S651, the procedure of the defined processing SUB1 starts. In step 3652, the value Ts/260 is substituted into Tsd. Ts is the pulse counter value of the stepping motor 111-1 that drives the SLO focus. Hence, dividing the value by 260 means substituting the value D on the relative coordinate system in which 0D corresponds to +15D into Tsd, as described above.

In step S653, it is determined whether Tsd falls within the range of 15 (inclusive) to 33 (inclusive). If Tsd falls within the range of 15 (inclusive) to 33 (inclusive), that is, if Tsd falls within the range of 0D (inclusive) to −18D (inclusive) on the absolute coordinate system, the process advances to step S654. In step S654, 1.2(−Tsd+15)+3.6 is substituted into Tod. In this case, Tod corresponds to the value Y of equation (6). The process advances to step S656. If Tsd does not fall within the range of 15 (inclusive) to 33 (inclusive), that is, if Tsd falls within the range of 0D (inclusive) to +18D (inclusive) on the absolute coordinate system, the process advances to step S655. In step S655, 0.76(−Tsd+15)+3.6 is substituted into Tod. In this case, Tod corresponds to the value Y of equation (5). The value Tod obtained in step S654 or S655 indicates the target point at which the OCT focus lens 123 is to be positioned, and the value is the value D on the absolute coordinate system. The process advances to step S656.

In step S656, −Tod+15 is substituted into Tot. Tot corresponds to Ds of equation (4). In this processing, the value Tod obtained in step S654 or S655 is substituted into Dz of equation (4) to obtain Ds, that is, Tot. The process advances to step S657.

In step S657, Tod×260 is substituted into Top. This is the pulse counter value of the target point set in step S654 or S655. The process advances to step S658.

In step S658, To−Top is substituted into Todiff. In step S658, the pulse counter value difference between the current position and the positioning target position of the OCT focus is obtained. The process advances to step S659.

In step S659, it is determined whether Todiff is 0 or more. If Todiff is positive, the process advances to step S661. In step S661, a Todiff pulse in the CW direction is sent to the stepping motor 123-1. The process advances to step S662. If Todiff is negative, the process advances to step S660. In step S660, a |Todiff| pulse in the CCW direction is sent to the stepping motor 123-1. In this case, ‖ means an absolute value. The process advances to step S662. In step S662, the value Top is substituted into To. The process advances to step S663. In step 3663, the defined processing is terminated.

As described above, the optical coherence tomographic imaging apparatus according to this embodiment can move the OCT focus lens that is an example of the second optical focus member in conjunction with the movement of the SLO focus lens that is an example of the first optical focus member. Since this shortens the time required for focus adjustment, the burden on the subject can be reduced. In another embodiment, the optical coherence tomographic imaging apparatus can move the OCT focus lens jointly with the movement of the SLO focus lens. In yet another embodiment, the optical coherence tomographic imaging apparatus can move the OCT focus lens simultaneously with the movement of the SLO focus lens.

In auto focus adjustment, first, the SLO focus lens is moved based on the light reception signal output from the light-receiving element. The OCT focus lens is moved based on the position information of the SLO focus lens and interlockingly with the movement of the SLO focus lens. At this time, the position information of the SLO focus lens can be acquired by a position information acquisition unit (not shown) before the start of the movement of the OCT focus lens. It is therefore possible to move the OCT focus lens based on the acquired position information.

At this time, the movement of the OCT focus lens may start before the movement of the SLO focus lens to the focus position is completed. Since this allows to further shorten the time required for focus adjustment, the burden on the subject can further be reduced.

In addition, the apparatus may start the movement of the OCT focus lens after completion of the first movement of the SLO focus lens and move the OCT focus lens interlockingly with the second movement of the SLO focus lens. The first movement is, for example, rough focus. Rough focus means, for example, moving the focus lens at a relatively long driving interval based on the contrast of the SLO image during auto focus. The second movement is, for example, fine focus after rough focus. Fine focus means, for example, moving the focus lens at a driving interval shorter than that in rough focus.

In the above-described embodiment, SUB1 that is the processing of moving the OCT focus lens is invoked before completion of rough focus of the SLO focus lens and before completion of fine focus (steps S612 and S619). That is, the movement of the lens 123 that is an example of the second optical focus member starts before completion of rough focus of the SLO focus lens and before completion of fine focus. This allows to quickly perform fine focus of OCT after SLO focus.

In the above embodiment, auto focus adjustment has been described. However, manual focus adjustment by the operator may be performed. In this case, the SLO focus lens and the OCT focus lens can be moved simultaneously. In the manual focus adjustment as well, the movement of the SLO focus lens may start before the start of the movement of the OCT focus lens, as a matter of course.

According to an embodiment, the SLO focus lens and the OCT focus lens can be moved jointly based on the SLO focus lens moving amount designated by a designation unit (not shown). According to another embodiment, the movement of the SLO focus lens and the movement of the OCT focus lens are simultaneously started based on the designated SLO focus lens moving amount. Since this allows to further shorten the time required for focus adjustment, the burden on the object can further be reduced.

The system may be configured to allow selection of auto focus adjustment or manual focus adjustment by a selection unit (not shown) to appropriately change the manner the focus adjustment is performed. The system may be configured to allow manual focus adjustment after auto focus adjustment to increase the convenience of focus adjustment for the operator.

Note that positioning of the second optical focus member (for example, lens 123) disposed in the optical interference system relative to the position of the first optical focus member (for example, lens 111) may be performed based on a predetermined table. A table creation unit (not shown) may create the predetermined table based on a normal eye database. The table creation unit (not shown) may create the table based on the diopter of an eye to be examined. This allows to appropriately change the tilt angle and the like in the table based on the diopter.

Note that the present invention is not limited to the above-described embodiment. For example, in the above-described embodiment, the imaged subject is an eye. However, the present invention is applicable to an object or subject other than an eye such as skin or an organ. In this case, the present invention can be applied as a medical apparatus such as an endoscope. Hence, the present invention can be understood as an optical coherence tomographic imaging apparatus exemplified by an ophthalmic apparatuses and the eye can be understood as a form of subject or object.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-190616, filed Aug. 30, 2012, which is hereby incorporated by reference herein in its entirety.

What is claimed is:

1. An optical coherence tomographic imaging apparatus comprising:
    an optical interference system configured to acquire a tomographic image of an object based on interference light between return light from the object irradiated with measurement light and reference light corresponding to the measurement light;
    an optical observation system that includes an optical illumination system configured to illuminate the object and a light-receiving optical system configured to cause a light-receiving element to receive return light from the object illuminated by the optical illumination system, and obtain an observed image of the object based on a light reception signal output from the light-receiving element;
    a first focus motor configured to move a first optical focus member disposed in the light-receiving optical system based on the light reception signal output from the light-receiving element; and
    a second focus motor configured to move a second optical focus member disposed in the optical interference system in conjunction with a movement of the first optical focus member.

2. The apparatus according to claim 1, wherein the second focus motor is configured to move the second optical focus member based on position information of the first optical focus member and in conjunction with the movement of the first optical focus member.

3. The apparatus according to claim 1, wherein the second focus motor is configured to start moving the second optical focus member before completion of the movement of the first optical focus member to a focus position.

4. The apparatus according to claim 1, wherein the second focus motor is configured to start moving the second optical focus member after completion of a first movement of the first optical focus member and move the second optical focus member in conjunction with a second movement of the first optical focus member.

5. The apparatus according to claim 1, wherein the second focus motor is configured to position the second optical focus member disposed in the optical interference system relative to a position of the first optical focus member based on a predetermined table.

6. The apparatus according to claim 5, wherein the object is an eye, and the apparatus further comprises a computer that, when operated, functions as a table creation unit configured to create the predetermined table based on a normal eye database.

7. The apparatus according to claim 5, wherein
the object is an eye, and
the apparatus further comprises a computer that, when operated, functions as a table creation unit configured to create the predetermined table based on a diopter of the eye.

8. The apparatus according to claim 1, wherein the second focus motor is configured to move the second focus optical member simultaneously with the movement of the first focus optical member.

9. The apparatus according to claim 1, wherein the second focus motor is controlled independently of the first focus motor.

10. The apparatus according to claim 1, wherein the second focus motor moves, based on the light reception signal output from the light-receiving element, the second optical focus member in conjunction with the movement of the first optical focus member.

11. A control method of an optical coherence tomographic imaging apparatus including an optical interference system that acquires a tomographic image of an object based on interference light between return light from the object irradiated with measurement light and reference light corresponding to the measurement light, and an optical observation system that includes an optical illumination system that illuminates the object and a light-receiving optical system that causes a light-receiving element to receive return light from the object illuminated by the optical illumination system, and obtains an observed image of the object based on a light reception signal output from the light-receiving element, the method comprising the steps of:
moving, by a first focus motor, a first optical focus member disposed in the light-receiving optical system based on the light reception signal output from the light-receiving element; and
moving, by a second focus motor, a second optical focus member disposed in the optical interference system in conjunction with a movement of the first optical focus member.

12. The method according to claim 11, wherein
in the step of moving the second optical focus member, the second optical focus member is moved based on position information of the first optical focus member and in conjunction with the movement of the first optical focus member.

13. The method according to claim 11, wherein in the step of moving the second optical focus member, a movement of the second optical focus member is started before completion of the movement of the first optical focus member to a focus position.

14. The method according to claim 11, wherein in the step of moving the second optical focus member, the movement of the second optical focus member is started after completion of a first movement of the first optical focus member, and the second optical focus member is moved in conjunction with a second movement of the first optical focus member.

15. The method according to claim 11, wherein in the step of moving the second optical focus member, the second optical focus member is moved simultaneously with the movement of the first optical focus member.

16. The method according to claim 11, wherein moving the first optical focus member is performed independently of moving the second optical focus member.

17. The method according to claim 11, wherein the second focus motor moves, based on the light reception signal output from the light-receiving element, the second optical focus member in conjunction with the movement of the first optical focus member.

18. A non-transitory computer-readable medium storing a program which upon execution by a computer causes the computer to execute each step of a control method of an optical coherence tomographic imaging apparatus including an optical interference system that acquires a tomographic image of an object based on interference light between return light from the object irradiated with measurement light and reference light corresponding to the measurement light, and an optical observation system that includes an optical illumination system that illuminates the object and a light-receiving optical system that causes a light-receiving element to receive return light from the object illuminated by the optical illumination system, and obtains an observed image of the object based on a light reception signal output from the light-receiving element, the method comprising the steps of:
moving a first optical focus member disposed in the light-receiving optical system based on the light reception signal output from the light-receiving element; and
moving a second optical focus member disposed in the optical interference system in conjunction with a movement of the first optical focus member.

19. The non-transitory computer-readable medium according to claim 18, wherein moving the first optical focus member is performed independently of moving the second optical focus member.

20. The non-transitory computer readable medium according to claim 18, wherein a second focus motor moves, based on the light reception signal output from the light-receiving element, the second optical focus member in conjunction with the movement of the first optical focus member.

21. The non-transitory computer-readable medium according to claim 18, wherein in the step of moving the second optical focus member, the second optical focus member is moved simultaneously with the movement of the first optical focus member.

22. An optical coherence tomographic apparatus comprising:
an optical interference system configured to acquire a tomographic image of an object based on interference light between return light from the object irradiated with measurement light and reference light corresponding to the measurement light;
an optical observation system that includes an optical illumination system configured to illuminate the object and a light-receiving optical system configured to cause a light-receiving element to receive the return light from the object illuminated by the optical illumination system, and obtain an observed image of the object based on a light reception signal output from the light-receiving element;
a first focus motor configured to move a first optical focus member disposed in the light-receiving optical system; and
a second focus motor configured to move a second optical focus member disposed in the optical interference system simultaneously with a movement of the first optical focus member.

23. The apparatus according to claim 22, wherein the second focus motor is controlled independently of the first focus motor.

24. The apparatus according to claim 22, wherein the first focus motor moves, based on the light reception signal output from the light-receiving element, the first optical focus member, wherein the second focus motor moves, based on the light reception signal output from the light-receiving element, the second optical focus member simultaneously with the movement of the first optical focus member.

25. A control method of an optical coherence tomographic imaging apparatus including an optical interference system that acquires a tomographic image of an object based on interference light between return light from the object irradiated with measurement light and reference light corresponding to the measurement light, and an optical observation system that includes an optical illumination system that illuminates the object and a light-receiving optical system that causes a light-receiving element to receive return light from the object illuminated by the optical illumination system, and obtains an observed image of the object based on a light reception signal output from the light-receiving element, the method comprising the steps of:

moving, by a first focus motor, a first optical focus member disposed in the light-receiving optical system; and moving, by a second focus motor, a second optical focus member disposed in the optical interference system simultaneously with a movement of the first optical focus member.

26. The method according to claim 25, wherein moving the first optical focus member is performed independently of moving the second optical focus member.

27. The method according to claim 25, wherein the first focus motor moves, based on the light reception signal output from the light-receiving element, the first optical focus member, wherein the second focus motor moves, based on the light reception signal output from the light-receiving element, the second optical focus member simultaneously with the movement of the first optical focus member.

28. A non-transitory computer-readable medium storing a program which upon execution by a computer causes the computer to execute each step of a control method of an optical coherence tomographic imaging apparatus including an optical interference system that acquires a tomographic image of an object based on interference light between return light from the object irradiated with measurement light and reference light corresponding to the measurement light, and an optical observation system that includes an optical illumination system that illuminates the object and a light-receiving optical system that causes a light-receiving element to receive return light from the object illuminated by the optical illumination system, and obtains an observed image of the object based on a light reception signal output from the light-receiving element, the method comprising the steps of:

moving a first optical focus member disposed in the light-receiving optical system; and moving a second optical focus member disposed in the optical interference system simultaneously with a movement of the first optical focus member.

29. The non-transitory computer-readable medium according to claim 28, wherein moving the first optical focus member is performed independently of moving the second optical focus member.

30. The non-transitory computer-readable medium according to claim 28, wherein the first focus motor moves, based on the light reception signal output from the light-receiving element, the first optical focus member, wherein the second focus motor moves, based on the light reception signal output from the light-receiving element, the second optical focus member simultaneously with the movement of the first optical focus member.

* * * * *